United States Patent [19]
Kawai et al.

[11] Patent Number: 5,654,489
[45] Date of Patent: Aug. 5, 1997

[54] PROCESS FOR PRODUCING ALICYCLIC DIKETONE COMPOUNDS

[75] Inventors: Shuji Kawai; Noboru Araki, both of Joyo; Hiroshi Itoh, Uji, all of Japan

[73] Assignee: New Japan Chemical Co., Ltd., Kyoto, Japan

[21] Appl. No.: 505,456

[22] Filed: Jul. 21, 1995

[30] Foreign Application Priority Data

Aug. 9, 1994 [JP] Japan .................................. 6-187441

[51] Int. Cl.$^6$ ............................................. C07C 45/00
[52] U.S. Cl. ............................................. 568/361; 568/363
[58] Field of Search ............................ 568/361, 363

[56] References Cited

U.S. PATENT DOCUMENTS

| | | | |
|---|---|---|---|
| 2,496,960 | 2/1950 | Schaefgen | 568/331 |
| 3,420,887 | 1/1969 | Noddings et al. | 568/361 |
| 3,586,720 | 6/1971 | Knepper et al. | 568/361 |
| 4,310,703 | 1/1982 | Tamaru et al. | 568/361 |
| 4,380,673 | 4/1983 | Boumonville et al. | 568/361 |
| 4,670,605 | 6/1987 | Chiu et al. | 568/361 |
| 4,918,239 | 4/1990 | Wang et al. | 568/361 |
| 5,227,530 | 7/1993 | Satek et al. | 568/361 |

OTHER PUBLICATIONS

Journal of the American Chemical Society, vol. 70, 1948, DC, US, pp. 2823–2824, J.R. Schaefgen et al, "Synthesis of an Octabasic Carboxylic Acid".

*Primary Examiner*—James H. Reamer
*Attorney, Agent, or Firm*—Larson & Taylor

[57] ABSTRACT

There is provided a process for producing an alicyclic diketone compound represented by the formula (1)

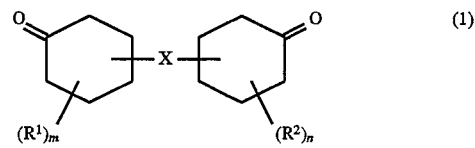

wherein X is a single bond, —$CH_2$—, —$C(CH_3)_2$—, —O— or —$SO_2$—, $R^1$ and $R^2$ each represents an alkyl group having 1 to 6 carbon atoms, m and n are 0 to 2, comprising dehydrogenating an alicyclic diol compound represented by the formula (2)

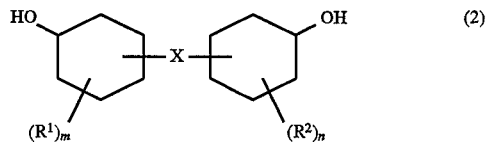

wherein X, $R^1$, $R^2$, m and n are as defined above in a liquid phase in the presence of at least one member selected from the group consisting of copper type catalysts and Raney type catalysts.

29 Claims, No Drawings

PROCESS FOR PRODUCING ALICYCLIC DIKETONE COMPOUNDS

FIELD OF THE INVENTION

The present invention relates to a process for producing alicyclic diketone compounds.

DESCRIPTION OF THE PRIOR ART

It is known to produce an alicyclic diketone compound by oxidizing an alicyclic diol with a reagent. For example, processes are known wherein 2,2-bis(4-hydroxycyclohexyl) propane is oxidized with chromic acid (Bull. Chem. Soc. Japan, 39(10), 2194(1966)) or with hypochlorous acid (Japanese Unexamined Patent Publication No. 59742/1992). However, according to these processes, the desired compound is obtained in an unsatisfactory yield with an unsatisfactory purity, and a large amount of waste such as metal salts derived from the oxidizing agent used is produced as by-products. Thus, they are industrially disadvantageous.

SUMMARY OF THE INVENTION

An object of the present invention is to solve the above problems of the prior art and to provide a process for producing an alicyclic diketone compound at a low cost, in a high yield and with a high purity.

The present inventors conducted extensive research to solve the above problems, and found that the contemplated object can be achieved by dehydrogenating an alicyclic diol compound in a liquid phase in the presence of a specific kind of catalyst. The present invention has been accomplished based on this finding.

Thus, the present invention provides a process for producing an alicyclic diketone compound represented by the formula (1)

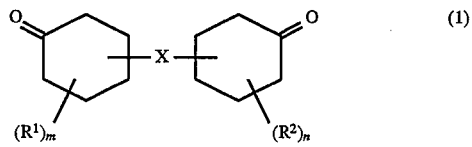

wherein X is a single bond, —CH$_2$—, —C(CH$_3$)$_2$—, —O— or —SO$_2$—, R$^1$ and R$^2$ are the same or different and each represents an alkyl group having 1 to 6 carbon atoms, m and n are the same or different and each represents an integer of 0 to 2, the process comprising subjecting an alicyclic diol compound represented by the formula (2)

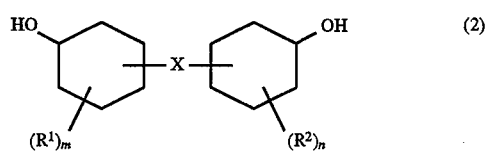

wherein X, R$^1$, R$^2$, m and n are as defined above to dehydrogenation in a liquid phase in the presence of at least one member selected from the group consisting of copper type catalysts and Raney type catalysts.

DETAILED DESCRIPTION OF THE INVENTION

The C$_1$ to C$_6$ alkyl group represented by R$^1$ and R$^2$ includes straight- or branched-chain C$_1$ to C$_6$ alkyl groups. Specific examples thereof are methyl, ethyl, n-propyl, isopropyl, n-butyl, t-butyl, n-hexyl and the like. Among them, preferred are C$_1$ to C$_4$ alkyl groups such as methyl, ethyl, n-propyl and t-butyl.

Of the compounds of the formula (1), preferable are those of the formula (1) wherein X is a single bond, —CH$_2$—, —C(CH$_3$)$_2$—, R$^1$ and R$^2$ are the same and each represents methyl, ethyl, n-propyl or t-butyl, m and n are the same and each represents an integer of 0 to 2. Particularly preferable are those of the formula (1) wherein X is a single bond or —C(CH$_3$)$_2$—, R$^1$ and R$^2$ are the same and each represents methyl or t-butyl, m and n are the same and each represents an integer of 0 or 1.

The compound of the formula (1) wherein X represents a single bond or —C(CH$_3$)$_2$— and m and n each represents 0 (i.e., R$^1$=R$^2$=H) are more preferable, and the compound of the formula (1) wherein X represents —C(CH$_3$)$_2$— and m and n each represents 0 (i.e., R$^1$=R$^2$=H) is the most preferable. These more preferable compounds are described, for example, in Bull. Chem. Soc. Japan, 39(10), 2194(1966), Japanese Unexamined Patent Publication No. 59742/1992 or U.S. Pat. No. 3,821,317.

Of the starting material to be used in the process according to the present invention, preferable are the alicyclic diol compounds represented by the formula (2) wherein X is a single bond, —CH$_2$—, —C(CH$_3$)$_2$—, R$^1$ and R$^2$ are the same and each represents methyl, ethyl, n-propyl or t-butyl, m and n are the same and each represents an integer of 0 to 2. Particularly preferable starting materials are those of the formula (2) wherein X is a single bond or —C(CH$_3$)$_2$—, R$^1$ and R$^2$ are the same and each represents methyl or t-butyl, m and n are the same and each represents an integer of 0 or 1.

The starting compound of the formula (2) wherein X represents a single bond or —C(CH$_3$)$_2$— and m and n each represents 0 (i.e., R$^1$=R$^2$=H) are more preferable, and the starting compound of the formula (2) wherein X represents —C(CH$_3$)$_2$— and m and n each represents 0 (i.e., R$^1$=R$^2$=H) is the most preferable.

Typical examples of the starting material of the formula (2) include, for example, bis(4-hydroxycyclohexyl), bis(2-methyl-4-hydroxycyclohexyl), bis(2-hydroxycyclohexyl), bis(4-hydroxycyclohexyl)methane, bis(2-ethyl-4-hydroxycyclohexyl)methane, bis(2-hydroxycyclohexyl) methane, (2-hydroxycyclohexyl)-(4-hydroxycyclohexyl) methane, 2,2-bis(4-hydroxycyclohexyl)propane, 2,2-bis(3,5-dimethyl-4-hydroxycyclohexyl)propane, 2,2-bis(3,5-di-t-butyl-4-hydroxycyclohexyl)propane, 2,2-bis(2-methyl-4-hydroxycyclohexyl)propane, 2,2-bis(2-hydroxycyclohexyl) propane, 2-(2-hydroxycyclohexyl)-2-(4-hydroxycyclohexyl)propane, bis(4-hydroxycyclohexyl) ether, bis(2-hydroxycyclohexyl) ether, bis(4-hydroxycyclohexyl) sulfone, bis(2-methyl-4-hydroxycyclohexyl) sulfone and the like. Especially recommended as effective starting materials are bis(4-hydroxycyclohexyl), 2,2-bis(4-hydroxycyclohexyl)propane and the like.

The alicyclic diol compound represented by the formula (2) is known or can be readily prepared by the method described in Japanese Unexamined Patent Publication (Kokai) No. 119855/1978 or No. 260034/1986, for example, by hydrogenating the corresponding diphenol compound of the following formula (I) in the presence of a hydrogenation catalyst, as shown in Reaction Scheme-1.

Reaction Scheme-1

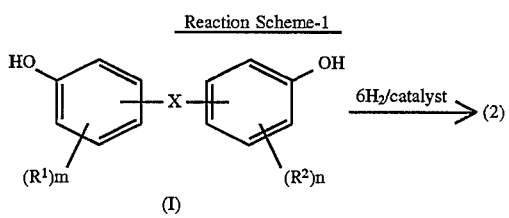

In the formula (I), X, $R^1$, $R^2$, m and n are as defined above.

The hydrogenation reaction according to the Scheme-1 can be conducted at a hydrogen pressure in the range of about 10 to about 150 kg/cm²G at a temperature of about 120° to 200° C. for about 5 to about 10 hours. The hydrogenation reaction may be conducted in the absence of a solvent. However, when the starting material represented by the formula (I) has a high melting point, a solvent such as methanol, ethanol or isopropanol may be used. The hydrogenation catalyst to be used are any of those conventionally used for hydrogenating benzene ring, and includes Ni-containing catalyst, Ru-containing catalyst and Pd-containing catalyst. The amount of the catalyst usually ranges from 0.5 to 2 wt. % based on the compound of the formula (I).

The compound of the formula (I) is also known or can be readily prepared from an alkyl-substituted phenol compound of the formula (II) by a known process, such as those illustrated in Schemes-A, B and C, wherein $R^1$ and m are as defined above.

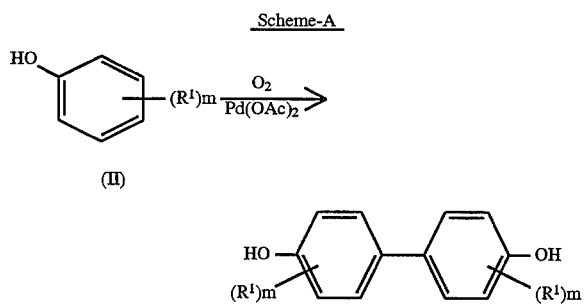

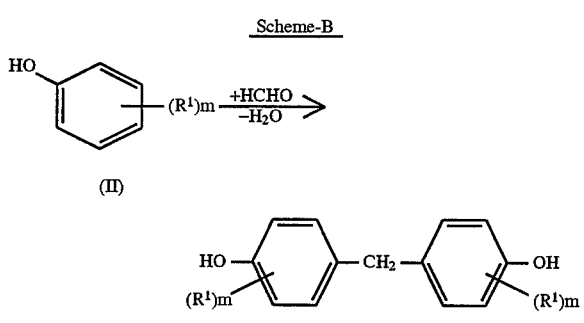

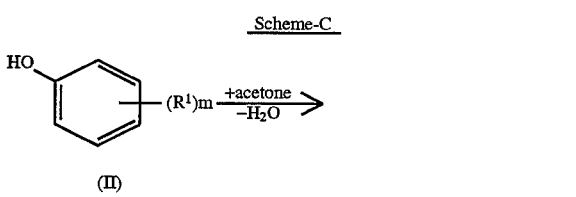

-continued
Scheme-C

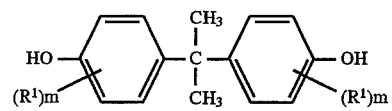

The reaction in Scheme-A is usually carried out in an oxygen-containing atmosphere such as air in the presence or absence of a solvent such as N,N-dimethylformamide or dimethylsulfoxide in the presence of a catalytic amount (usually about 0.5 to about 1 wt. % based on the compound of the formula (II)) of a palladium acetate catalyst at a temperature of about 130° to 180° C. and at a reaction pressure of about 30 to about 50 kg/cm²G for about 4 to about 10 hours, as described in Japanese Unexamined Patent Publications (Kokai) Nos. 52749/1973 and 153747/1980.

The reactions in Schemes-B and C are usually carried out using about 0.5 to about 0.6 moles of formaldehyde or acetone per mole of the phenol compound (II) in the presence or absence of an acid catalyst such as sulfuric acid, hydrochloric acid or phosphoric acid at a temperature of about 50° to 150° C. and at a reaction pressure of about 0 to about 1 kg/cm²G for about 3 to about 5 hours, as described in Chemical Industry, 11, 567 (1960) published by Kagaku Kogyosha, Inc., Japan. In this reaction, excess phenol compound (II) also acts as a reaction solvent.

According to the present invention, it is important to use at least one catalyst selected from the group consisting of copper type catalysts and Raney type catalysts for the dehydrogenation. Other catalysts such as palladium type catalysts, ruthenium type catalysts and rhodium type catalysts are expensive, and the use of these other catalysts gives a large amount of by-products and results in an unsatisfactory yield of the desired compound.

The copper type catalysts include copper-containing mixed catalyst, copper oxide-containing mixed catalyst and a modified catalyst of these mixed catalyst.

Typically, there may be mentioned (a) a mixed catalyst containing copper and at least one metal selected from the group consisting of zinc and chromium, (b) a mixed catalyst containing a copper oxide and at least one oxide selected from the group consisting of a zinc oxide and a chromium oxide, (c-a) a modified catalyst wherein molybdenum, tungsten, magnesium, barium, aluminum, calcium, zirconium, cobalt, manganese, nickel or the like or a mixture of at least two of these metals is admixed with the above mixed catalyst (a), and (c-b) a modified catalyst wherein a molybdenum oxide, tungsten oxide, magnesium oxide, barium oxide, aluminum oxide, calcium oxide, zirconium oxide, cobalt oxide, manganese oxide, nickel oxide or the like or a mixture of at least two of these metal oxides is admixed with the above mixed catalyst (b).

In modified catalysts (c-a) and (c-b), preferred metal to be admixed with mixed catalyst (a) is barium or calcium, and preferred metal oxide to be admixed with mixed catalyst (b) is barium oxide or calcium oxide.

Specific examples of the copper type catalysts, particularly mixed catalyst (b) or modified catalyst (c-b), include zinc oxide-chromium oxide-copper oxide, zinc oxide-chromium oxide-copper oxide-magnesium oxide, zinc oxide-chromium oxide-copper oxide-barium oxide, zinc oxide-copper oxide, zinc oxide-copper oxide-magnesium oxide, zinc oxide-copper oxide-aluminum oxide, copper oxide-chromium oxide, copper oxide-chromium oxide-magnesium oxide, copper oxide-chromium oxide-barium oxide, copper oxide-chromium oxide-manganese oxide, copper oxide-chromium oxide-barium oxide-manganese oxide and the like.

Among them, so-called Adkins catalysts such as copper oxide-chromium oxide, copper oxide-chromium oxide-magnesium oxide, copper oxide-chromium oxide-barium oxide, copper oxide-chromium oxide-manganese oxide, copper oxide-chromium oxide-barium oxide-manganese oxide and the like are generally preferred. The copper oxide-chromium oxide is more preferable.

Specific examples of mixed catalyst (a) and modified catalyst (c-a) are those composed of the metals contained in mixed catalyst (b) and modified catalyst (c-b) exemplified above. Among them, copper-zinc catalyst and copper-chromium catalyst are preferred.

The amount of the copper or copper oxide of these copper type catalysts is not particularly limited, but it is generally preferable that the above mixed catalyst (a) contain 20 to 80 wt. %, preferably 40 to 60 wt. %, of copper relative to the weight of said mixed catalyst (a), and that the above mixed catalyst (b) contain 20 to 80 wt. %, preferably 40 to 60 wt. %, of copper oxide relative to the weight of said mixed catalyst (b).

In the above modified catalysts (c-a), said metal such as molybdenum, tungsten, magnesium, barium, aluminum, calcium, zirconium, cobalt, manganese, nickel or the like or a mixture of at least two of these metals may be used in an amount of 0.5 to 20 wt. %, preferably 1 to 10 wt. %, based on the weight of the mixed catalyst (a). In the above modified catalysts (c-b), said oxide such as molybdenum oxide, tungsten oxide, magnesium oxide, barium oxide, aluminum oxide, calcium oxide, zirconium oxide, cobalt oxide, manganese oxide, nickel oxide or the like or a mixture of at least two of these metal oxides may be used in an amount of 0.5 to 20 wt. %, preferably 1 to 10 wt. %, based on the weight of the mixed catalyst (b).

The above copper type catalysts are known or can be readily obtained by a known method, such as a conventional precipitation method or a conventional kneading method.

Typically, the precipitation method usually comprises the steps of providing an aqueous solution of a water-soluble copper salt (such as copper sulfate, copper nitrate or copper chloride) and a water-soluble salt (such as sulfate, nitrate or hydrochloride) of the metal other than copper, such as zinc, chromium, molybdenum or the like, adding an alkali such as ammonia water, sodium hydroxide or potassium hydroxide to the solution to adjust the pH of the solution and to thereby cause co-precipitation, and calcining the resulting precipitate in air at a high temperature of about 300° to about 350° C. for about 5 to about 10 hours, whereby the above mixed catalyst (b) or modified catalyst (c-b) is prepared. Furthermore, various MnO- and/or BaO-modified copper oxide-chromium oxide mixed catalysts are also commercially available.

The kneading method generally comprises the steps of mixing a powder of a copper salt (e.g., copper sulfate, copper nitrate or copper chloride) with an aqueous solution of a water-soluble salt (such as sulfate, nitrate or hydrochloride) of the metal other than copper, such as zinc, chromium, molybdenum or the like, and kneading the mixture while evaporating the water therein, drying the mixture and calcining the dried mixture in air at a high temperature of about 400° to about 600° C. for about 5 to about 10 hours, whereby the above mixed catalyst (b) or the modified catalyst (c-b) is prepared.

In particular, said copper oxide-chromium oxide catalyst ($CuO \cdot CuCr_2O_4$) can be prepared in the same manner as in the preparation of the known Adkins catalyst. For example, an aqueous solution containing sodium bichromate and ammonia is added with stirring to an aqueous solution of copper nitrate or copper sulfate to form a precipitate, and calcining the precipitate in air at about 400° C. for about 5 to about 10 hours. Said copper oxide-chromium oxide catalyst ($CuO \cdot CuCr_2O_4$) is also commercially available.

Mixed catalyst (a) and modified catalyst (c-a) can be prepared by treating mixed catalyst (b) and modified catalyst (c-b) in a powder form, respectively, with a hydrogen stream under atmospheric pressure at 150°–300° C., by the method described, for example, in "SESSHOKU SUISOKA HANNOU (Catalytic hydrogenation reaction)", page 29 authored by Shigeo Nishimura and Yuzuru Takagi and published in 1987 by Tokyo Kagaku Dojin, Japan.

Furthermore, the above copper type catalysts, especially mixed catalyst (a) or (b), may be used as placed or deposited on a support such as silica, alumina, diatomaceous earth, clay, carbon, graphite or the like, wherein the amount of said mixed catalyst generally ranges from about 1 to 10 wt. % relative to the weight of the support.

The Raney type catalysts that can be used in the invention include, for example, Raney nickel, Raney cobalt, Raney cobalt-manganese, Raney copper and the like, which are now commercially manufactured. Among them, Raney cobalt and Raney cobalt-manganese are preferable, and Raney cobalt is more preferable.

These Raney type catalysts are prepared by leaching the aluminum from an alloy of aluminum and the metal component thereof such as nickel, cobalt, cobalt-manganese or copper by means of an alkali such as sodium hydroxide in a conventional manner.

It is preferable that the amount of aluminum contained in the metal-aluminum alloy before leaching for preparing the Raney type catalysts is about 40 to 70 wt. %, preferably about 50 to 60 wt. %.

The copper type catalysts and Raney type catalysts may be used as such.

Alternatively, the copper type catalysts may be subjected beforehand to an appropriate activation treatment such as reduction using a reducing agent such as hydrogen, sodium boron hydride, lithium aluminum hydride, sodium aluminum hydride and the like, and then used for the reaction. Such activation treatment can be conducted in a conventional manner, for example, by mixing the copper type catalyst in the form of a powder with an aliphatic alcohol such as methanol, ethanol or n-butanol to prepare a slurry, and treating the slurry with hydrogen at a temperature of about 150° to about 250° C. at a hydrogen pressure of about 100 to 200 kg/cm$^2$G for about 2 to 4 hours.

The Raney type catalysts are usually obtained in a water-containing state or in a hydrated form. It is recommended to replace the water, before use, by a solvent which is the same solvent as used in the reaction or by a solvent which is fully dissolved in water and inert to the reaction such as methanol, ethanol or other aliphatic lower alcohol, dioxane, diethylene glycol, diethylene glycol dimethyl ether or other ether. This treatment for replacing the water with such a solvent is carried out in a conventional manner, for example, by repeating about 2 to 5 cycles of a treatment which comprises the steps of adding an excess amount of said solvent to the water-containing Raney catalyst (hydrated form), stirring the mixture at room temperature for about 1–5 minutes and removing the solvent.

The form of the catalyst is not limited specifically, and may be a powder form, tablet form or the like, depending on the mode of the reaction. Especially recommended for the copper type catalyst is a tablet form for use as a fixed catalyst bed.

The catalyst is usually used in an amount of about 0.1 to 30 wt. %, preferably about 1 to 20 wt. %, based on the alicyclic diol compound of the formula (2) to be used as the starting material. If the amount of the catalyst is less than 0.1 wt. %, it is often difficult to obtain a reaction rate sufficient for practical use. On the other hand, the use of more than 30 wt. % of the catalyst does not remarkably improve the effects and thus it is economically disadvantageous.

As mentioned, the Raney type catalysts are usually obtained in a water-containing state, and the above amounts of the catalyst to be used are based on the amount calculated as dry weight.

The above copper type catalyst and Raney type catalyst can be used repeatedly.

The dehydrogenation reaction of the process of the present invention is carried out in a liquid phase.

Thus, the dehydrogenation reaction can be carried out in the absence of a solvent at a temperature of higher than the melting point of the starting material of the formula (2), and preferably lower than 300° C., so that the starting material of the formula (2) will be used in a molten state.

However, in order to maintain the catalyst activity and in order to obtain the desired alicyclic diketone compound in an improved yield, it is preferred to carry out the reaction in a solvent. Especially when the starting material and the product have a high melting point, it is recommended to use a solvent to facilitate handling.

Any solvents which are inert to the reaction and can readily dissolve the starting material and the product are usable. Specific examples include ethers, hydrocarbons and ketones.

Examples of the ethers include ethylene glycol dimethyl ether, ethylene glycol diethyl ether, ethylene glycol dipropyl ether, ethylene glycol dibutyl ether, diethylene glycol dimethyl ether, diethylene glycol diethyl ether, diethylene glycol dipropyl ether, ethylene glycol dibutyl ether, triethylene glycol dimethyl ether and the like. Among them, recommended are ethylene glycol dimethyl ether and diethylene glycol dimethyl ether, which are readily available commercially and have a high dissolving power.

Examples of the hydrocarbons include, for example, aromatic hydrocarbons such as benzene, toluene, xylene, polyalkyl benzene, particularly benzene substituted with 1 to 3 alkyl groups having 1 to 6 carbon atoms; alicyclic hydrocarbons such as cyclohexane, methylcyclohexane, dimethylcyclohexane, polyalkylcyclohexane, particularly cyclohexane substituted with 1 to 3 alkyl groups having 1 to 6 carbon atoms; etc. Among them, benzene substituted with 1 to 3 alkyl groups having 1 to 3 carbon atoms and cyclohexane substituted with 1 to 3 alkyl groups having 1 to 3 carbon atoms are recommended, since they are readily available commercially, have a high boiling point and are easy to handle.

Examples of the ketones include, for example, acetone, methyl ethyl ketone, diethyl ketone, diisopropyl ketone, dibutyl ketone, diisobutyl ketone, cyclohexanone and the like. Among them, recommended are methyl ethyl ketone, di(n-butyl)ketone and diisobutyl ketone which are readily available commercially, have a high boiling point and are easy to handle.

The above solvents can be used singly, or at least two of them can be used in combination.

A suitable amount of the solvent is 0.05 to 10 times, preferably 0.2 to 3 times, the weight of the alicyclic diol compound of the formula (2). If the amount is less than 0.05 times the weight of said alicyclic diol compound, it is generally difficult to maintain the activity of the catalyst used and to dissolve a starting material having a high melting point. On the other hand, the use of the solvent in an amount of more than 10 times the weight of the compound tends to be economically disadvantageous.

A recommended temperature for the dehydrogenation reaction is 160° to 300° C., especially 200° to 240° C. If the temperature is lower than 160° C., it is often difficult to obtain a reaction rate sufficient for practical use, while a temperature higher than 300° C. is not preferred since a secondary reaction tends to occur pronouncedly.

A suitable range of the reaction pressure varies depending on the presence or absence of the solvent and the kind of the solvent to be used.

When a solvent is not used in the dehydrogenation reaction, the reaction can be carried out at atmospheric pressure (in an open system), if the reaction temperature is lower than the boiling point, but higher than the melting point, of the alicyclic diol compound of the formula (2) used as the starting material. If the reaction temperature is equal to or higher than the boiling point of said alicyclic diol compound, the reaction is carried out under pressure (in a closed system). Hydrogen generated during the reaction acts as a factor inhibiting the reaction. Therefore, especially when the reaction is carried out under pressure, it is preferred to continuously or intermittently expel or purge the generated hydrogen from the reaction system so as to prevent the partial pressure of hydrogen from increasing.

When a solvent is used in the dehydrogenation reaction, the reaction is basically carried out under pressure. A suitable pressure varies depends on the reaction temperature and the kinds of the solvent, starting material and product. Specifically stated, the pressure of 0.1 to 20 kg/cm$^2$G is recommended. If the pressure is less than 0.1 kg/cm$^2$G, the reaction temperature will not rise and thus it is often difficult to obtain a reaction rate sufficient for practical use. On the other hand, a pressure of more than 20 kg/cm$^2$G is not preferable partly because the partial pressure of hydrogen is likely to increase irrespective of the kind of the solvent, and partly because a secondary reaction tends to occur pronouncedly. In this case, too, it is preferred to continuously or intermittently expel or purge the generated hydrogen together with the solvent from the reaction system so as to prevent the partial pressure of hydrogen from increasing.

Preferably, the solvent is continuously or intermittently supplied to the reaction system to maintain the amount of the solvent at the start of the reaction. In such a case, it is preferred to collect the solvent expelled or purged from the reaction system and recycle the collected solvent to the system. However, fresh solvent may be supplied to the reaction system.

For expelling or purging the hydrogen generated during the reaction, an inert gas such as nitrogen is preferably used as a carrier gas to promote the reaction. This effect is remarkable especially when the reaction is carried out in the absence of a solvent.

The amount of the inert gas to be introduced is not limited specifically insofar as the contemplated effect can be produced, but it is recommended to use the inert gas per unit time in a volume of 0.01 to 50 times, preferably 0.1 to 10 times, the average volume of the hydrogen generated per unit time. If the volume of the inert gas is less than 0.1 times the average volume of the generated hydrogen, the effect of expelling the hydrogen is very small. On the other hand, if the inert gas is used in excess of 50 times the volume of the generated hydrogen, the effect of expelling the hydrogen will not increase appreciably and therefore economically disadvantageous; and the starting material and by-products tend to be markedly entrained.

The reaction time varies depending on the conditions, but is usually about 0.5 to 20 hours.

The dehydrogenation reaction can be carried out as a batchwise or continuous suspension reaction using a powdery catalyst, or as a reaction using a tablet form catalyst in a fixed bed reactor.

The crude reaction product thus obtained may be isolated, for example, by separating the catalyst from the reaction mixture by filtration, and evaporating the solvent from the filtrate under reduced pressure.

The thus-obtained crude product may be purified, if so desired, by distillation or recrystallization to thereby give a purified product.

According to the process of the present invention, an alicyclic diketone compound can be produced at a low cost, in a high yield and with a high purity. The diketone compound produced by the process of the present invention is useful as a starting material for medicaments, as a starting material for industrial chemicals, as a starting material for polymers, as a starting material for polymerization initiators and the like, and as an intermediate for preparing antioxidants, heat resistance improvers and the like.

EXAMPLES

The following Examples are further illustrative of the present invention. The product obtained in each example was checked for the purity of the desired substance by the internal standard method using a gas chromatography (GC) technique and by the measurement of the carbonyl value as determined by the method according to JIS K 1525.

Example 1

A 500 ml-autoclave equipped with a magnetic stirrer was charged with 50 g of bis(4-hydroxycyclohexyl) as a starting material, 150 g of diethylene glycol dimethyl ether as a reaction solvent and 2 g of a Raney cobalt-manganese catalyst (formulation of the alloy before leaching (wt. %) was Co:Mn:Al=30:4:66). The water contained in the Raney cobalt-manganese catalyst had previously been replaced by diethylene glycol dimethyl ether.

The air in the reaction system was replaced by hydrogen at atmospheric pressure. The reaction system was then heated to 230° C., and the dehydrogenation reaction was carried out for 8 hours under the pressure of 1.8 kg/cm$^2$G while continuously releasing the generated hydrogen with one of the valves of the autoclave kept slightly open. The diethylene glycol dimethylether entrained in the released hydrogen gas was collected and recycled to the reaction system by means of a high-pressure pump so as to maintain the original liquid level at the start of the reaction.

After completion of the reaction, the reaction mixture was cooled, withdrawn from the autoclave, and diluted with and dissolved in diethylene glycol dimethylether. The catalyst was filtered off and the solvent was removed under reduced pressure, giving 48.0 g of a crude reaction product.

The purity of bis (4-oxocyclohexyl) in the obtained crude product was found to be 88.5% (yield: 86.7%). The carbonyl value of the crude product was 520 (theoretical value=578).

Example 2

A dehydrogenation reaction was carried out for 6 hours in the same manner as in Example 1 with the exception of using 50 g of 2,2-bis(4-hydroxycyclohexyl)propane as the starting material and 5 g of a Raney cobalt catalyst (formulation of the alloy before leaching (wt. %) was Co:Al=49:51) as the catalyst.

Then, the resulting reaction mixture was worked up following the procedure of Example 1, giving 47.0 g of a crude reaction product.

The purity of 2,2-bis(4-oxocyclohexyl)propane in the crude reaction product was found to be 92.2% (yield: 88.1%). The carbonyl value of the crude product was 441 (theoretical value=475).

Example 3

Following the procedure of Example 1 and using 50 g of 2,2-bis(2-methyl-4-hydroxycyclohexyl)propane as the starting material, 100 g of alkylbenzene solvent (trade name "Solvesso 150", $C_{10}$-$C_{11}$ fraction content=92%, product of EXXON CHEMICAL CO., LTD.) as the solvent, and 3 g of a modified copper oxide-chromium oxide catalyst (formulation (wt. %)=CuO:Cr$_2$O$_3$:BaO:MnO=48:46:2:4), a dehydrogenation reaction was carried out at 220° C. under the pressure of 0.3 kg/cm$^2$G for 6 hours.

The reaction mixture was worked up in the same manner as in Example 1, giving 47.5 g of a crude reaction product. The purity of 2,2-bis(2-methyl-4-oxocyclohexyl)propane in the crude product was found to be 86.5% (yield 83.3%). The carbonyl value of the crude product was 369 (theoretical value=425).

Said modified catalyst was prepared by the method described in "SESSHOKU SUISOKA HANNOU (Catalytic hydrogenation reaction)", page 29, authored by Shigeo Nishimura and Yuzuru Takagi and published in 1987 by Tokyo Kagaku Dojin, Japan.

Example 4

A dehydrogenation reaction was carried out for 7 hours in the same manner as in Example 2 with the exception of using 50 g of bis(4-hydroxycyclohexyl)methane as the starting material. The reaction mixture was worked up in the same manner as in Example 2, giving 47.8 g of a crude reaction product.

It was found that the purity of bis(4-oxocyclohexyl) methane in the crude product was 85.6% (yield: 83.4%). The carbonyl value of the crude product was 465 (theoretical value=539).

Example 5

A dehydrogenation reaction was carried out for 5 hours in the same manner as in Example 2 with the exception of using 50 g of bis(4-hydroxycyclohexyl) ether as the starting material. The reaction mixture was worked up in the same manner as in Example 2, giving 47.3 g of a crude reaction product.

It was found that the purity of bis(4-oxocyclohexyl) ether in the crude product was 92.5% (yield: 89.2%). The carbonyl value of the crude product was 502 (theoretical value= 534).

Example 6

A dehydrogenation reaction was carried out for 9 hours in the same manner as in Example 1 with the exception of using 50 g of bis(4-hydroxycyclohexyl) sulfone as the starting material and 3 g of powdery zinc oxide-copper oxide as the catalyst (formulation of the catalyst (wt. %) was ZnO:CuO=48:52). The reaction mixture was worked up in the same manner as in Example 1, giving 46.2 g of a crude reaction product.

It was found that the purity of bis(4-oxocyclohexyl) sulfone in the crude product was 82.0% (yield: 76.9%). The carbonyl value of the crude product was 362 (theoretical value=435).

Example 7

A dehydrogenation reaction was carried out for 8 hours in the same manner as in Example 1 except that 150 g of di(n-butyl) ketone was used as the solvent and that the pressure applied to the system was 2.0 kg/cm$^2$G. The reaction mixture was worked up in the same manner as in Example 1, giving 47.4 g of a crude reaction product.

It was found that the purity of bis(4-oxocyclohexyl) in the crude product was 89.5% (yield: 86.6%). The carbonyl value of the crude product was 521.

Example 8

A dehydrogenation reaction was carried out for 10 hours in the same manner as in Example 1 except that any solvent was not used. Hydrogen generated during the reaction was continuously expelled by keeping the valve of the autoclave slightly open. The reaction mixture was worked up in the same manner as in Example 1, giving 46.0 g of a crude reaction mixture.

It was found that the purity of bis(4-oxocyclohexyl) in the crude product was 81.5% (yield: 76.5%). The carbonyl value of the crude product was 475.

Example 9

A dehydrogenation reaction was carried out in the same manner as in Example 8 except that a nitrogen gas was introduced into the autoclave at a rate of 2 liter/hour to continuously expel the hydrogen formed during the reaction. The reaction mixture was worked up in the same manner as in Example 8, giving 46.9 g of a crude reaction product.

It was found that the purity of bis(4-oxocyclohexyl) in the crude product was 95.2% (yield: 91.1%). The carbonyl value of the crude product was 555.

Example 10

A dehydrogenation reaction was carried out in the same manner as in Example 2 except that the pressure applied to the system was increased to 5 kg/cm$^2$G. The reaction mixture was worked up in the same manner as in Example 2, giving 46.1 g of a crude reaction product.

It was found that the purity of 2,2-bis(4-oxocyclohexyl) propane in the crude product was 75.2% (yield: 70.5%). The carbonyl value of the crude product was 363.

Example 11

A dehydrogenation reaction was carried out in the same manner as in Example 2 except that the reaction temperature was set at 270° C. The reaction mixture was worked up in the same manner as in Example 2, giving 43.2 g of a crude reaction product.

It was found that the purity of 2,2-bis(4-oxocyclohexyl) propane in the crude product was 72.5% (yield: 63.7%). The carbonyl value of the crude product was 352.

Example 12

A dehydrogenation reaction was carried out in the same manner as in Example 2 with the exception of using 1 g of copper oxide-chromium oxide catalyst (formulation (wt. %)=CuO:Cr$_2$O$_3$=35:65) and 100 g of a commercially available xylene mixture (o-xylene:m-xylene:p-xylene:ethylbenzene=20:45:20:15 wt. %) as the solvent and conducting the reaction at 240° C. under the pressure of 6 kg/cm$^2$G for 8 hours.

The reaction mixture was worked up in the same manner as in Example 2, giving 47.9 g of a crude reaction product. The purity of 2,2-bis(4-oxocyclohexyl)propane in the crude product was found to be 94.5% (yield 92.1%). The carbonyl value of the crude product was 452.

Example 13

A dehydrogenation reaction was carried out in the same manner as in Example 12 with the exception of using 50 g of bis(4-hydroxycyclohexyl)methane as the starting material. The reaction mixture was worked up in the same manner as in Example 12, giving 46.8 g of a crude reaction product.

It was found that the purity of bis(4-oxocyclohexyl) methane in the crude product was 89.5% (yield: 85.4%). The carbonyl value of the crude product was 491.

Example 14

A dehydrogenation reaction was carried out in the same manner as in Example 12 with the exception of using 50 g of bis(4-hydroxycyclohexyl) ether as the starting material. The reaction mixture was worked up in the same manner as in Example 12, giving 48.2 g of a crude reaction product.

It was found that the purity of bis(4-oxocyclohexyl) ether in the crude product was 93.2% (yield: 91.5%). The carbonyl value of the crude product was 502.

Comparative Example 1

A dehydrogenation reaction was carried out in the same manner as in Example 2 with the exception of using 5% Ru/Al$_2$O$_3$ (5 parts by weight of Ru placed on 100 parts by weight of an Al$_2$O$_3$ support) as the catalyst. The reaction mixture was worked up in the same manner as in Example 2, giving 47.2 g of a crude reaction product.

It was found that the purity of 2,2-bis(4-oxocyclohexyl) propane in the crude reaction product was as low as 60.2% (yield: 57.7%). The carbonyl value of the crude product was 291.

Comparative Example 2

A dehydrogenation reaction was carried out in the same manner as in Example 2 with the exception of using 5% Pd/carbon (5 parts by weight of Pd placed on 100 parts by weight of a carbon support) as the catalyst. The reaction mixture was worked up in the same manner as in Example 2, giving 44.2 g of a crude reaction product.

It was found that the purity of 2,2-bis(4-oxocyclohexyl) propane in the crude reaction product was as low as 35.3% (yield: 31.7%). The carbonyl value of the crude product was 171.

Comparative Example 3

A dehydrogenation reaction was carried out in the same manner as in Example 2 with the exception of using 5% Rh/carbon (5 parts by weight of Rh placed on 100 parts by weight of a carbon support) as the catalyst. The reaction mixture was worked up in the same manner as in Example 2, giving 46.3 g of a crude reaction product.

It was found that the purity of 2,2-bis(4-oxocyclohexyl) propane was as low as 45.3% (yield: 42.6%). The carbonyl value of the crude product was 223.

Unlike the reagent oxidization method presently employed for industrial purpose, the process of the present invention can provide the desired alicyclic diketone compound without producing by-products to be disposed of as a waste. Furthermore, according to the process of the present invention, the desired compound can be obtained at a low cost in a high yield and a high selectivity, under industrially advantageous conditions.

We claim:

1. A process for producing an alicyclic diketone compound represented by the formula (1)

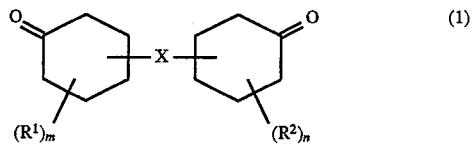

wherein X is a single bond, —$CH_2$—, —$C(CH_3)_2$—, —O— or —$SO_2$—, $R^1$ and $R^2$ are the same or different and each represents an alkyl group having 1 to 6 carbon atoms, m and n are the same or different and each represents an integer of 0 to 2, the process comprising subjecting an alicyclic diol compound represented by the formula (2)

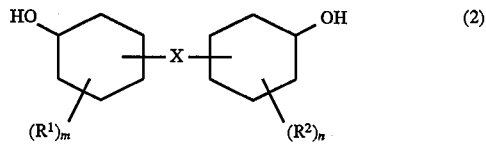

wherein X, $R^1$, $R^2$, m and n are as defined above to dehydrogenation in a liquid phase in the presence of at least one catalyst selected from the group consisting of copper type catalysts and Raney type catalysts, with the proviso that Raney nickel type catalysts are excluded, wherein the dehydrogenation is carried out in the presence of a solvent selected from the group consisting of ethers, hydrocarbons and ketones, wherein the ethers are selected from the group consisting of ethylene glycol dimethyl ether, ethylene glycol diethyl ether, ethylene glycol dipropyl ether, ethylene glycol dibutyl ether, diethylene glycol dimethyl ether, diethylene glycol diethyl ether, diethylene glycol dipropyl ether, triethylene glycol dimethyl ether.

2. The process according to claim 1 wherein in the formulas (1) and (2), X is a single bond, —$CH_2$—, —$C(CH_3)_2$—, $R^1$ and $R^2$ and are the same and each represents methyl, ethyl, n-propyl or t-butyl, m and n are the same and each represents an integer of 0 to 2.

3. The process according to claim 1 wherein in the formulas (1) and (2), X represents a single bond or —$C(CH_3)_2$— and m and n each represents 0.

4. The process according to claim 1 wherein in the formulas (1) and (2), X represents —$C(CH_3)_2$— and m and n each represents 0.

5. The process according to claim 1 wherein the catalyst is a copper type catalyst.

6. The process according to claim 5 wherein the catalyst is (a) a mixed catalyst containing copper and at least one metal selected from the group consisting of zinc and chromium, (b) a mixed catalyst containing a copper oxide and at least one oxide selected from the group consisting of a zinc oxide and a chromium oxide, (c-a) a modified catalyst wherein at least one metal selected from the group consisting of molybdenum, tungsten, magnesium, barium, aluminum, calcium, zirconium, cobalt, manganese and nickel is admixed with the above mixed catalyst (a), or (c-b) a modified catalyst wherein at least one metal oxide selected from the group consisting of molybdenum oxide, tungsten oxide, magnesium oxide, barium oxide, aluminum oxide, calcium oxide, zirconium oxide, cobalt oxide, manganese oxide and nickel oxide is admixed with the above mixed catalyst (b).

7. The process according to claim 6 wherein the mixed catalyst (a) contains 20 to 80 wt. % of copper relative to the weight of said mixed catalyst (a), and the mixed catalyst (b) contains 20 to 80 wt. % of copper oxide relative to the weight of said mixed catalyst (b).

8. The process according to claim 6 wherein said at least one metal selected from the group consisting of molybdenum, tungsten, magnesium, barium, aluminum, calcium, zirconium, cobalt, manganese and nickel in the modified catalysts (c-a) is used in an amount of 0.5 to 20 wt. % based on the weight of the mixed catalyst (a).

9. The process according to claim 6 wherein said at least one metal oxide selected from the group consisting of molybdenum oxide, tungsten oxide, magnesium oxide, barium oxide, aluminum oxide, calcium oxide, zirconium oxide, cobalt oxide, manganese oxide and nickel oxide in the above modified catalysts (c-b) is used in an amount of 0.5 to 20 wt. % based on the weight of the mixed catalyst (b).

10. The process according to claim 5 wherein said copper type catalysts is at least one member selected from the group consisting of zinc oxide-chromium oxide-copper oxide, zinc oxide-chromium oxide-copper oxide-magnesium oxide, zinc oxide-chromium oxide-copper oxide-barium oxide, zinc oxide-copper oxide, zinc oxide-copper oxide-magnesium oxide, zinc oxide-copper oxide-aluminum oxide, copper oxide-chromium oxide, copper oxide-chromium oxide-magnesium oxide, copper oxide-chromium oxide-barium oxide, copper oxide-chromium oxide-manganese oxide and copper oxide-chromium oxide-barium oxide-manganese oxide.

11. The process according to claim 5 wherein said copper type catalysts is at least one member selected from the group consisting of copper oxide-chromium oxide, copper oxide-chromium oxide-magnesium oxide, copper oxide-chromium oxide-barium oxide, copper oxide-chromium oxide-manganese oxide and copper oxide-chromium oxide-barium oxide-manganese oxide.

12. The process according to claim 5 wherein said copper type catalysts is copper oxide-chromium oxide.

13. The process according to claim 5 wherein said mixed catalyst (a) or (b) is placed or deposited on a support selected from the group consisting of silica, alumina, diatomaceous earth, clay, carbon and graphite.

14. The process according to claim 1 wherein the catalyst is a Raney type catalyst, with the proviso that Raney nickel type catalysts are excluded.

15. The process according to claim 14 wherein the Raney type catalyst is at least one member selected from the group consisting of Raney cobalt, Raney cobalt-manganese and Raney copper.

16. The process according to claim 14 wherein the Raney type catalyst is at least one member selected from the group consisting of Raney cobalt and Raney cobalt-manganese.

17. The process according to claim 14 wherein the Raney type catalyst is Raney cobalt.

18. The process according to claim 1 wherein the catalyst is used in an amount of 0.1 to 30% by weight based on the compound of the formula (2).

19. The process according to claim 1 wherein the dehydrogenation is carried out at a temperature of 160° to 300° C.

20. The process according to claim 1 wherein the dehydrogenation is carried out for about 0.5 to 20 hours.

21. The process according to claim 1 wherein the solvent is used in an amount of about 0.05 to 10 times the weight of the alicyclic diol compound represented by the formula (2).

22. The process according to claim 1 wherein the dehydrogenation is carried out while expelling or purging the generated hydrogen together with the solvent from the reaction system so as to prevent the partial pressure of hydrogen from increasing.

23. The process according to claim 1 wherein the dehydrogenation is carried out under pressure.

24. The process according to claim 1 wherein the dehydrogenation is carried out at a pressure of 0.1 to 20 kg/cm$^2$G.

25. The process according to claim 1 wherein the solvent is selected from the group consisting of di($C_1$–$C_4$ alkyl) ether of ethylene glycol, of diethylene glycol or of triethylene glycol.

26. The process according to claim 1 wherein the solvent is benzene, benzene substituted with 1 to 3 alkyl groups having 1 to 6 carbon atoms, cyclohexane or cyclohexane substituted with 1 to 3 alkyl groups having 1 to 6 carbon atoms.

27. The process according to claim 1 wherein the solvent is benzene substituted with 1 to 3 alkyl groups having 1 to 3 carbon atoms or cyclohexane substituted with 1 to 3 alkyl groups having 1 to 3 carbon atoms.

28. The process according to claim 1 wherein the solvent is acetone, methyl ethyl ketone, diethyl ketone, diisopropyl ketone, dibutyl ketone, diisobutyl ketone or cyclohexanone.

29. The process according to claim 1 wherein the solvent is used in an amount of about 0.2 to 3 times the weight of the alicyclic diol compound represented by the formula (2).

* * * * *